(12) United States Patent
Huang et al.

(10) Patent No.: US 11,110,201 B2
(45) Date of Patent: Sep. 7, 2021

(54) DEVICES INCLUDING MUSCLE MATRIX AND METHODS OF PRODUCTION AND USE

(71) Applicant: LifeCell Corporation, Branchburg, NJ (US)

(72) Inventors: Li Ting Huang, Branchburg, NJ (US); Eric Stec, Washington, NJ (US); Nathaniel Bachrach, Clifton, NJ (US); Hui Xu, Plainsboro, NJ (US)

(73) Assignee: LifeCell Corporation, Madison, NJ (US)

( * ) Notice: Subject to any disclaimer, the term of this patent is extended or adjusted under 35 U.S.C. 154(b) by 47 days.

(21) Appl. No.: 15/881,911

(22) Filed: Jan. 29, 2018

(65) Prior Publication Data

US 2018/0214603 A1    Aug. 2, 2018

Related U.S. Application Data

(60) Provisional application No. 62/451,981, filed on Jan. 30, 2017.

(51) Int. Cl.
*A61L 27/36* (2006.01)
*A61L 27/16* (2006.01)
(Continued)

(52) U.S. Cl.
CPC ........ *A61L 27/3604* (2013.01); *A61F 2/0063* (2013.01); *A61F 2/08* (2013.01);
(Continued)

(58) Field of Classification Search
CPC ............ A61F 2/0063; A61F 2002/2835; A61F 2/105; A61F 2/08; A61F 2002/0894; A61F 2002/0081; A61L 27/3604; A61L 27/367; A61L 27/3687; A61L 27/58; A61L 27/3691; A61L 27/3873; A61L 27/18; A61L 27/3645; A61L 27/16; A61L 27/50; A61L 27/56; A61L 27/3683; A61L 27/04; A61L 2430/30
See application file for complete search history.

(56) References Cited

U.S. PATENT DOCUMENTS 5,336,616 A    8/1994  Livesey et al.
5,364,756 A    11/1994 Livesey et al.
(Continued)

FOREIGN PATENT DOCUMENTS

CN    1266716 A     9/2000
CN    101361989 A   2/2009
(Continued)

OTHER PUBLICATIONS

Aberle et al., Cell-Type Specific Four Component Hydrogel, PLOS One, Jan. 2014, vol. 9, Issue 1, e86740.
(Continued)

*Primary Examiner* — Brian A Dukert
*Assistant Examiner* — Rebecca Lynee Zimmerman
(74) *Attorney, Agent, or Firm* — McCarter & English, LLP

(57) ABSTRACT

Tissue compositions and methods of preparation thereof are provided. The tissue compositions can be used to treat or regenerate muscle tissue. The compositions can be configured to provide increased strength compared to other muscle matrices.

7 Claims, 9 Drawing Sheets

(51) Int. Cl.

| | | |
|---|---|---|
| *A61L 27/50* | (2006.01) | |
| *A61L 27/56* | (2006.01) | |
| *A61F 2/00* | (2006.01) | |
| *A61F 2/08* | (2006.01) | |
| *A61L 27/04* | (2006.01) | |
| *A61L 27/58* | (2006.01) | |
| *A61L 27/38* | (2006.01) | |
| *A61L 27/18* | (2006.01) | |

(52) U.S. Cl.
CPC ............... *A61L 27/04* (2013.01); *A61L 27/16* (2013.01); *A61L 27/18* (2013.01); *A61L 27/367* (2013.01); *A61L 27/3645* (2013.01); *A61L 27/3683* (2013.01); *A61L 27/3687* (2013.01); *A61L 27/3691* (2013.01); *A61L 27/3873* (2013.01); *A61L 27/50* (2013.01); *A61L 27/56* (2013.01); *A61L 27/58* (2013.01); *A61F 2002/0081* (2013.01); *A61F 2002/0894* (2013.01); *A61L 2430/30* (2013.01)

(56) References Cited

U.S. PATENT DOCUMENTS

| | | | |
|---|---|---|---|
| 6,166,288 | A | 12/2000 | Diamond et al. |
| 6,381,026 | B1 | 4/2002 | Schiff et al. |
| 6,933,326 | B1 | 8/2005 | Griffey et al. |
| 7,358,284 | B2 | 4/2008 | Griffey et al. |
| 7,883,541 | B2 | 2/2011 | Mills et al. |
| 8,415,125 | B2 | 4/2013 | Fujisato et al. |
| 9,044,455 | B2 * | 6/2015 | Shah .................. A61L 27/3695 |
| 9,382,422 | B2 | 7/2016 | Owens et al. |
| 2003/0035843 | A1 | 2/2003 | Livesey et al. |
| 2003/0143207 | A1 | 7/2003 | Livesey et al. |
| 2005/0028228 | A1 | 2/2005 | McQuillan et al. |
| 2006/0073592 | A1 | 4/2006 | Sun et al. |
| 2006/0127375 | A1 | 6/2006 | Livesey et al. |
| 2006/0210960 | A1 | 9/2006 | Livesey et al. |
| 2007/0009586 | A1 | 1/2007 | Cohen et al. |
| 2007/0248575 | A1 | 10/2007 | Connor et al. |
| 2008/0027562 | A1 | 1/2008 | Fujisato et al. |
| 2009/0130221 | A1 | 5/2009 | Bolland et al. |
| 2009/0306790 | A1 | 12/2009 | Sun |
| 2010/0063539 | A1 * | 3/2010 | Yang .................. A61L 24/0005 606/214 |
| 2010/0233235 | A1 | 9/2010 | Matheny et al. |
| 2011/0021753 | A1 | 1/2011 | Huang |
| 2011/0054588 | A1 | 3/2011 | Ku et al. |
| 2011/0293666 | A1 * | 12/2011 | Wang .................. A61L 27/3804 424/400 |
| 2012/0010728 | A1 | 1/2012 | Sun et al. |
| 2012/0276213 | A1 | 11/2012 | Chen |
| 2014/0004549 | A1 | 1/2014 | Chen et al. |
| 2014/0088701 | A1 | 3/2014 | Sun et al. |
| 2014/0377833 | A1 | 12/2014 | Chen et al. |
| 2015/0282925 | A1 * | 10/2015 | Xu ........................ A61L 27/362 623/14.13 |
| 2016/0184478 | A1 | 6/2016 | Griffiths et al. |
| 2019/0298885 | A1 * | 10/2019 | Schilling ............. A61L 27/3895 |

FOREIGN PATENT DOCUMENTS

| | | |
|---|---|---|
| CN | 103805555 A | 5/2014 |
| WO | 1999/44533 A1 | 9/1999 |
| WO | 2001/091671 A1 | 12/2001 |
| WO | 2003/097694 A1 | 11/2003 |
| WO | 2005/009134 A1 | 2/2005 |
| WO | 2007/043513 A1 | 4/2007 |
| WO | 2007/110634 A2 | 10/2007 |
| WO | 2009/009620 A2 | 1/2009 |

OTHER PUBLICATIONS

Badylak et al., "Extracellular matrix as a biological scaffold material: Structure and function," Acta Biomaterials, vol. 5, pp. 1-13, Jan. 2009.

Collins et al., "Cardiac Xenografts Between Primate Species Provide Evidence for the Importance of the a-Galactosyl Determinant in Hyperacute Rejection," J. Immunol., vol. 154, pp. 5500-5510, May 1995.

Corona et al., Challenges to acellular biological scaffold mediated skeletal muscle tissue regeneration, Biomaterials 104 (Jul. 2016) 238-246.

Dequach et al.; "Injectable skeletal muscle matrix hydrogel promotes neovascularization and muscle cell infiltration in a hindlimb ischemia model—NIH Public Access;" Eur. Cell Mater.; 23:400-412 (Jun. 5, 2013).

Dobrin et al., "Elastase, collagenase, and the biaxial elastic properties of dog carotid artery," Am. J. Physiol. Heart Circ. Physiol., vol. 247, pp. H124-H131, Jul. 1984.

Galili et al., "Interaction between Human Natural Anti-a-Galactosyl Immuglobulin G and Bacteria of the Human Flora," Infection and Immunity, vol. 56, pp. 1730-1737, Jul. 1988.

Galili et al., "Man, Apes, and Old World Monkeys Differ from other Mammals in the Expression of a-Galctosyl Epitopes on Nucleated Cells," Journal of Biological Chemistry, vol. 263, No. 33, pp. 17755-17762, Nov. 1988.

Galili, Uri, "Interaction of the natural anti-Gal antibody with a-galactosyl epitopes: a major obstacle for xenotransplantation in humans," Immunology Today, vol. 14, pp. 480-482, Oct. 1993.

Good et al., "Identification of Carbohydrate Structures That Bind Human Antiporcine Antibodies: Implications for Discordant Xenografting in Humans," Transplant Proc., vol. 24, pp. 559-562, Apr. 1992.

Hamadeh et al., "Human Natural Anti-Gal IgG Regulates Alternative Complement Pathway Activation on Bacterial Surfaces," J. Clin. Invest., vol. 89, pp. 1223-1235, Apr. 1992.

International Search Report and Written Opinion for PCT/US2018/015686 dated Jul. 13, 2018 pp. 1-21.

Invitation to Pay Additional Fees and, Where Applicable, Protest Fee for International Application PCT/US2018/015686 dated May 18, 2018. pp. 1-46.

Ionescu et al., "Effect of Papain and Bromelin on Muscle and Collagen Proteins in Beef Meat," the Annals of the University Dunarea de Jos of Galati, Fasccile VI, Food Technology, New Series, pp. 9-16, Jul. 2008.

Lu et al., "Novel porous aortic elastin and collagen scaffolds for tissue engineering," Biomaterials, vol. 25, No. 22, pp. 5227-5237, Oct. 2004.

Merritt et al., "Functional Assessment of Skeletal Muscle Regeneration Utilizing Homologous Extracellular Matrix as Scaffolding," Tissue Engineering, vol. 16, No. 4, Part A, pp. 1395-1405, Jan. 2010.

Reihsner et al., "Biomechanical properties of elastase treated palmar aponeuroses," Connective Tissue Research, Vo. 26, pp. 77-86, Jan. 1991.

Sandrin et al., Anti-pig IgM antibodies in human serum react predominantly with Gal(a1-3)Gal epitopes, Proc. Natl. Acad. Sci., vol. 90, pp. 11391-11395, Dec. 1993.

Stern et al.; "The influence of extracellular matrix drived from skeletal muscle tissue on the proliferation and differentiation of myogenic progenitor cells ex vivo;" Biomaterials—Elsevier Science Publishers; 30(12):2393-2399 (Apr. 1, 2009).

Tedder et al., "Stabilized Collagen Scaffolds for Heart Valve Tissue Engineering," Tissue Engineering, vol. 00, Part A, pp. 1-12, Oct. 2008.

Turner et al., "Regeneration of skeletal muscle," Cell Tissue Res, vol. 347, No. 3, pp. 759-774, Mar. 2012.

Valentin, et al., "Functional skeletal muscle formation with a biologic scaffold," Biomaterials, vol. 31, No. 9, pp. 7475-7484, Oct. 2010.

Wang et al., Decellularized musculofascial extracellular matrix for tissue engineering, Biomaterials 34 (Jan. 2013) 2641-2654.

Wolf et al.; "Biologic scaffold composed of skeletal muscle extracellular matrix;" Biomaterials—Elsevier Science Publishers; 33(10):2916-2925 (Dec. 31, 2011).

(56) References Cited

OTHER PUBLICATIONS

Xu et al., "A Porcine-Derived Acellular Dermal Scaffold That Supports Soft Tissue Regeneration: Removal of Terminal Galactose-a-(1,3)-Galactose and Retention of Matrix Structure," Tissue Engineering, vol. 15, pp. 1-13, Jan. 2009.

Yuan et al., "Effects of collagenase and elastase on the mechanical properties of lung tissue strips," J. App. Physiol., Vo. 89, pp. 3-14, Jul. 2000.

\* cited by examiner

DEVICES INCLUDING MUSCLE MATRIX AND METHODS OF PRODUCTION AND USE

This application claims priority under 35 USC § 119 to U.S. Provisional Application No. 62/451,981, which was filed on Jan. 30, 2017 and is herein incorporated by reference in its entirety.

The present disclosure relates to tissue products, and more particularly, to tissue matrices produced from muscle tissue.

Various injuries, diseases, and surgical procedures result in the loss of muscle mass, particularly skeletal muscle. For example, surgical removal of soft tissue sarcomas and osteosarcomas can result in the loss of bulk muscle. Other surgical and cosmetic procedures, such as hernia repair and muscle augmentation, require long-term management of muscle content. Muscle damage can also result from injury, such as from blunt force trauma and gunshot injuries.

Current muscle regenerative procedures focus on the use of muscle allografts (e.g., harvesting gluteus maximus muscle from donor sites on the patient or from a cadaver) and the use of xenografts comprising completely decellularized dermal or other tissue matrices. However, the use of muscle transplants can lead to excess inflammation (resulting in scar tissue formation and potential rejection) and, if harvested from a patient, presents the problem of muscle loss at the donor site.

Currently, partially decellularized matrices can be produced for effective muscle treatment. However, these matrices may not support sufficient loads and may break down under stress. Thus, a need remains for improved methods and compositions for muscle treatment or regeneration.

Taught herein is a method of preparing a tissue composition. The method includes providing a tissue sample wherein the tissue sample comprises a muscle portion and a fascia portion harvested without separating the muscle portion of the tissue from the fascia portion of the tissue. The method also includes processing the tissue sample to produce at least one decellularized musculofascial matrix.

Taught herein is a tissue composition comprising at least one decellularized muscle matrix and at least one decellularized fascia matrix. The muscle matrix and the fascia matrix comprise at least one muscle tissue and at least one connected fascia tissue harvested without separating the muscle tissue from the fascia tissue. The muscle matrix contains at least some of the myofibers normally found in an unprocessed muscle sample.

Taught herein is a method of preparing a tissue composition including providing a muscle sample and processing the muscle sample to produce a decellularized muscle matrix wherein myofibers of the muscle matrix are oriented in a longitudinal direction.

Taught herein is a tissue composition comprising at least one decellularized muscle matrix that contains at least some of the myofibers normally found in an unprocessed muscle sample and wherein the myofibers are oriented longitudinally.

Taught herein is a method of preparing a tissue composition including providing a group of muscle matrices and layering and joining the group of muscle matrices to produce a multi-layer muscle matrix.

Taught herein is a tissue composition comprising multiple layers of decellularized muscle matrix that contain at least some of the myofibers normally found in an unprocessed muscle sample.

Taught herein is a method of preparing a tissue composition including selecting a muscle matrix layer and selecting a supporting layer. The method also includes applying a slurry comprising particulate acellular tissue matrix (ATM) to at least one of the muscle matrix layers or the supporting layer. The method also includes joining the muscle matrix layer and the supporting layer using the slurry.

Taught herein is a tissue composition including at least one muscle matrix layer and at least one supporting layer. The tissue composition also includes at least one particulate acellular tissue matrix (ATM) that attaches the at least one muscle layer to the at least one supporting layer.

Taught herein is a method of preparing a tissue composition. The method includes selecting a muscle matrix layer and selecting a supporting layer including one or more pores. The method includes applying a slurry comprising particulate acellular tissue matrix (ATM) to at least one of the muscle matrix layers or the supporting layer. The method includes applying the supporting layer to a first surface of the muscle matrix layer. The method also includes rolling the muscle matrix layer and the supporting layer such that at least a portion of the first surface of the muscle matrix layer attaches to at least a portion of a second surface of the muscle matrix layer through the one or more pores.

DESCRIPTION OF CERTAIN EXEMPLARY EMBODIMENTS

Figure 1:
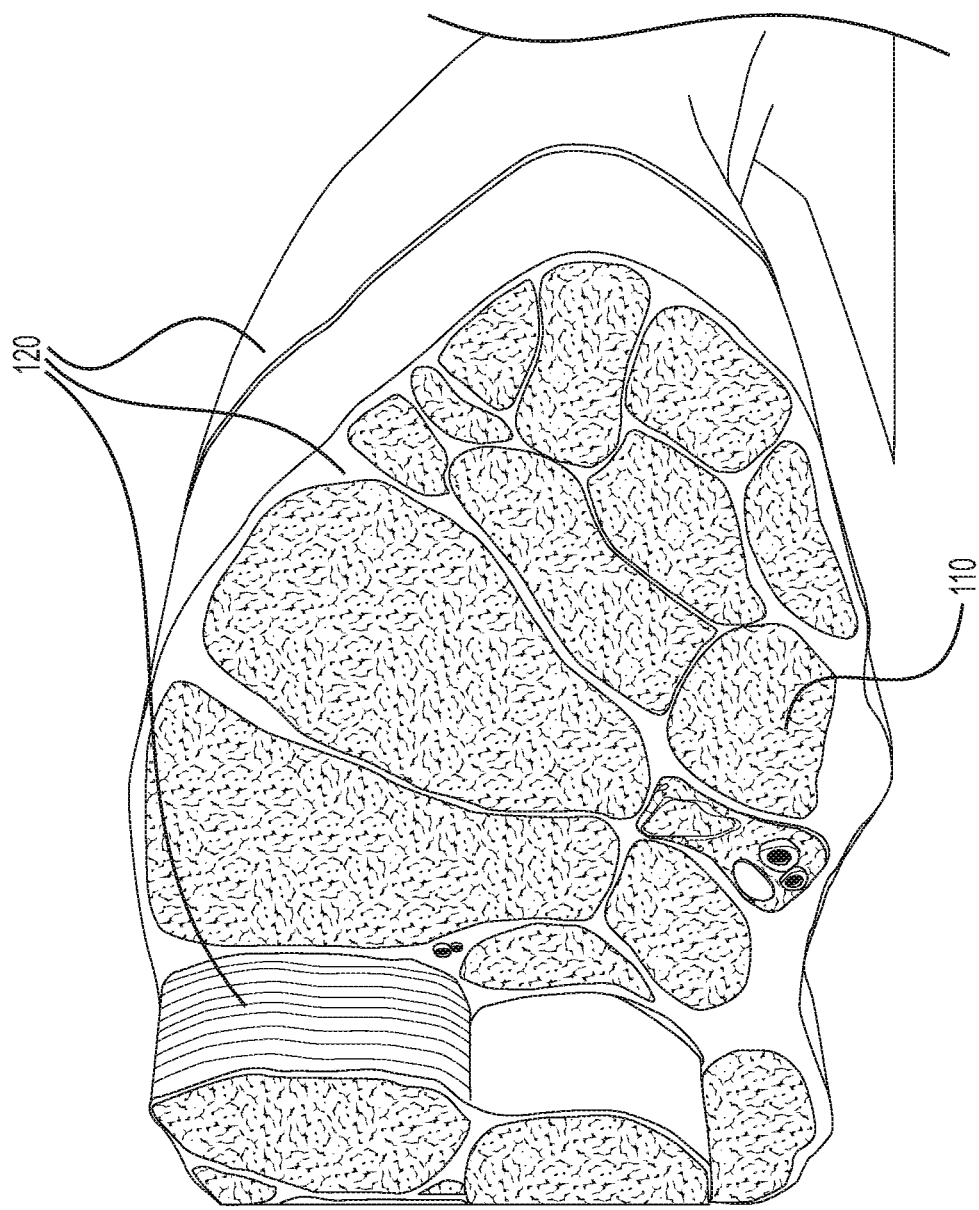
FIG. 1 illustrates a perspective view of a muscle and fascia tissue source that may be harvested to create a tissue product.
Figure 1:
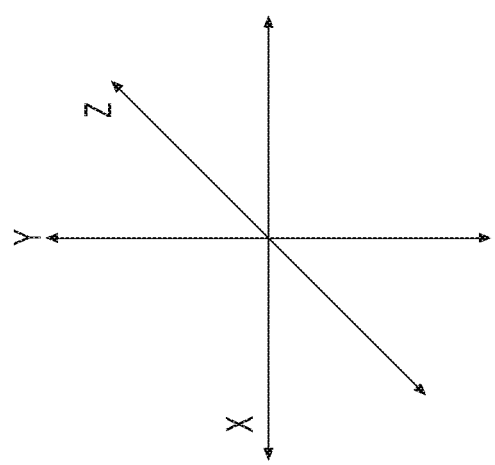

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

As used herein, "myofibers" are the rod-like structures involved in muscle contraction and comprise proteins such as myosin, troponin, tropomyosin, and actinin. Long myofiber chains are found in and between the elongated muscle cells (myocytes).

As used herein, a "muscle defect" is any muscle abnormality or damage that is amenable to repair, improvement, enhancement, regeneration, amelioration, and/or treatment by an implanted muscle matrix. A muscle defect encompasses any abnormality or damage resulting from disease, trauma, or surgical intervention that results in an alteration to the muscle. As used herein, the removal or loss of "bulk" muscle tissue refers to the loss of an appreciable and measurable volume of muscle tissue, e.g., a volume of at least about 0.5 $cm^3$.

As used herein, a "decellularized tissue" is any tissue from which most or all of the cells that are normally found growing in the extracellular matrix of the tissue have been removed (e.g., a tissue lacking about 80, 85, 90, 95, 99, 99.5, or 100% of the native cells, or any percentage in between).

The materials and methods provided herein can be used to make a biocompatible implant. As used herein, a "biocompatible" implant is a composition that has the ability to support the migration and proliferation of native cells from surrounding tissue into the composition following implantation and that does not elicit a substantial immune response that prevents such cellular activity. As used herein, a "substantial immune response" is one that prevents partial or complete resorption of the implanted material and/or the partial or complete repopulation of the implant with native cells.

As used herein, the terms "native cells" and "native tissue" mean the cells and tissue present in the recipient tissue or organ prior to the implantation of a muscle implant, or the cells or tissue produced by the host animal after implantation.

FIG. 1 is a perspective view of a muscle and fascia tissue source that may be harvested to create a tissue sample. In an exemplary tissue source, muscle tissue 110 is surrounded by fascia tissue 120. The tissue source may be any human or animal skeletal muscle and accompanying fascia that is suitable for decellularization and subsequent implantation in a treatment site. Once implanted, the decellularized musculofascial matrix produced from the tissue source can provide increased strength to the implanted region and/or can promote in-growth of muscle cells and regeneration of muscle tissue.

In exemplary embodiments, tissue compositions and decellularized musculofascial matrices described herein can have a higher initial strength than those known previously and can withstand higher loads without tearing. In some embodiments, the fascia matrix can provide a scaffold into which native cells (e.g., fibroblasts, etc.) can migrate, allowing for the remodeling of fascia and/or dermis along with the remodeled muscle induced by the muscle matrix.

In certain embodiments, the tissue sample comprises a muscle portion and a fascia portion harvested without separating the muscle portion 110 of the tissue from the fascia portion 120 of the tissue (including some or all of the surrounding fascia). Harvesting muscle tissue with surrounding fascia tissue enables the preparation of a tissue composition that can withstand a higher max load than a tissue composition composed of solely or predominately muscle tissue. Preparation of a muscle matrix is described in more detail below and is also described in pending U.S. application Ser. No. 14/410,204, filed on Dec. 22, 2014 and published as US Patent Publication US2015/0282925, which is incorporated herein by reference in its entirety.

In various embodiments, the tissue sample can be processed to remove blood or blood components such as red blood cells. For example, the tissue sample can be exposed to a cell lysis solution to remove cells such as red blood cells. A variety of blood cell removal or lysis solutions can be used, including, for example, solutions such as ammonium chloride, hypo- or hypertonic-saline, detergents, or other know blood removal compositions. Further, the solutions can be used in a number of incubation and/or wash steps, including for example, one to ten wash steps, or any suitable number in between.

In various embodiments, the tissue sample can be processed to produce a decellularized musculofascial matrix. For example, the tissue sample can be exposed to a decellularization solution in order to remove viable and non-viable cells from the muscle tissue without damaging the biological and/or structural integrity of an extracellular matrix within the muscle tissue. The decellularization solution may contain an appropriate buffer, salt, an antibiotic, one or more detergents (e.g., TRITON X100™ or other nonionic octylphenol ethoxylate surfactants, sodium dodecyl sulfate (SDS), sodium deoxycholate, or polyoxyethylene (20) sorbitan monolaurate), one or more agents to prevent cross-linking, one or more protease inhibitors, and/or one or more enzymes. In some embodiments, the decellularization solution can comprise 0.1%, 0.2%, 0.3%, 0.4%, 0.5%, 1.0%, 1.5%, 2.0%, 2.5%, 3.0%, 3.5%, 4.0%, 4.5%, 5.0%, or any intermediate percentage of TRITON X-100™ and, optionally, 10 mM, 15 mM, 20 mM, 25 mM, 30 mM, 35 mM, 40 mM, 45 mM, 50 mM, or any intermediate concentration of EDTA (ethylenediaminetetraacetic acid). In certain embodiments, the decellularization solution can comprise 0.1%, 0.2%, 0.3%, 0.4%, 0.5%, 1.0%, 1.5%, 2.0%, 2.5%, 3.0%, 3.5%, 4.0%, 4.5%, 5.0%, or any intermediate percentage of sodium deoxycholate and, optionally, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, or 20 mM HEPES buffer (4-(2-hydroxyethyl)-1-piperazineethanesulfonic acid) containing 10 mM, 15 mM, 20 mM, 25 mM, 30 mM, 35 mM, 40 mM, 45 mM, 50 mM, or any intermediate concentrations of EDTA. In some embodiments, the muscle tissue can be incubated in the decellularization solution at 20, 21, 22, 23, 24, 25, 30, 31, 32, 33, 34, 35, 36, 37, 38, 39, 40, 41, or 42 degrees Celsius (or any temperature in between), and optionally, gentle shaking can be applied at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, 48, 60, 72, 84, or 96 hours (or any time period in between).

The length of time of exposure to the decellularization solution and/or the concentration of detergent or other decellularizing agents can be adjusted in order to control the extent of decellularization and myofiber removal from the muscle tissue. In certain embodiments, additional detergents may be used to remove cells from the muscle tissue. For example, in some embodiments, sodium deoxycholate, SDS, and/or TRITON X-100™ can be used to decellularize and separate undesired tissue components from the extracellular tissue matrix.

In some embodiments, the tissue sample can be contacted with a solution including trypsin in order to break down muscle fiber bundles (e.g., by cleaving myosin molecules in the muscle fiber). In some embodiments, the solution can include additional enzymes such as papain, bromelain, ficin, or alcalase. In some embodiments, trypsin can facilitate the decellularization process by increasing the rate and/or extent of myofiber breakdown and myocyte removal during subsequent decellularization. In some embodiments, the muscle sample can be exposed to trypsin at a concentration in a range from about $10^{-10}$-0.5% (e.g., at about 0.02, 0.03, 0.04, 0.05, 0.06, 0.07, 0.08, 0.09, 0.1, 0.15, 0.2, 0.25, 0.3, 0.35, 0.4, 0.45, or 0.5 percent), or from $10^{-8}$-$10^{-4}$%, or from $10^{-7}$-$10^{-5}$%, or any percent inbetween. The aforementioned concentrations can be considered appropriate for enzymes that have an enzymatic activity such that $10^{-6}$% corresponds to approximately 120-130 BAEE units, and a BAEE unit is determined for enzymes with a specification for trypsin activity using Nα-Benzoyl-L-arginine ethyl ester (BAEE) as a substrate. The procedure is a continuous spectrophotometric rate determination (ΔA253, Light path=1 cm) based on the following reaction:

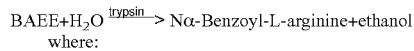

BAEE+H$_2$O $\xrightarrow{\text{trypsin}}$ Nα-Benzoyl-L-arginine+ethanol where:

BAEE=Nα-Benzoyl-L-arginine ethyl ester; and

A BAEE Unit is defined such that one BAEE unit of trypsin activity will produce a ΔA253 of 0.001 per minute with BAEE as substrate at pH 7.6 at 25° C. in a reaction volume of 3.20 ml.

A number of suitable trypsins may be used, but one exemplary trypsin that may be appropriate include bovine pancreatic trypsin, e.g., from Sigma Aldrich (Sigma-Aldrich product T1426).

In certain embodiments, the muscle sample can be exposed to trypsin for at least about 15 minutes or up to a maximum of about 24 hours (e.g., about 15 minutes, 30 minutes, 45 minutes, 60 minutes, 75 minutes, 90 minutes, 105 minutes, 120 minutes, 4 hours, 8 hours, 12 hours, 24 hours or any intermediate time). In certain embodiments, muscle samples including fascia can be exposed to trypsin for at least about 15 minutes or up to a maximum of about 48 hours (e.g., about 15 minutes, 30 minutes, 45 minutes, 60 minutes, 75 minutes, 90 minutes, 105 minutes, 120 minutes, 4 hours, 8 hours, 12 hours, 24 hours, 48 hours or any intermediate time). In various embodiments, decellularization can be done before trypsinization, after trypsinization, or both before and after trypsinization.

The procedure to decellularize the tissue sample can, in some embodiments, be controlled to retain at least some myofibers normally found in the tissue sample prior to processing. For example, the length of exposure and/or the concentration of the decellularization solution and/or trypsin solution can be adjusted in order to control the extent of myofiber removal. In some embodiments, the duration and/or concentration are selected in order to remove about 20-80% of the myofibers normally found in the muscle tissue prior to trypsinization and decellularization. In certain embodiments, the duration and/or concentration are selected in order to remove about 20, 30, 40, 50, 60, 70, 80, or 90 percent of the myofibers (or any percentage in between). In some embodiments, about 20-80% of the myofibers are removed by exposing the tissue sample to trypsin at a concentration ranging from $10^{-10}$-0.5% for 15 minutes to 24 or 48 hours and/or by exposing the muscle tissue sample to about 0.1-2.0% of a decellularization agent (e.g., TRITON X-100™ or other nonionic octylphenol ethoxylate surfactant, sodium dodecyl sulfate, sodium deoxycholate, or polyoxyethylene (20) sorbitan monolaurate) for 0.1-72 hours.

In other embodiments, the procedure to decellularize the tissue sample while retaining at least some myofibers normally found in the tissue sample prior to processing can be controlled by adjusting the ratio of tissue mass to volume of decellularization or trypsinization solution (e.g., the mass of tissue per volume of solution containing trypsin and/or decellularizing agents). In some embodiments, a lower ratio tissue to volume of solution can increase the efficiency of the myofiber removal process, thus resulting in a decellularized musculofascial matrix that retains fewer intact myofibers. In other embodiments, a higher ratio of tissue to volume of solution ratio can reduce the efficiency of the myofiber removal process, thus resulting in a decellularized musculofascial matrix that retains more intact myofibers.

In various embodiments, the extracellular scaffold within a decellularized muscle or musculofascial tissue may include collagen (particularly collagen type I or type III), elastin, myofiber, and/or other fibers, as well as proteoglycans, polysaccharides, and/or growth factors (e.g. IGF, EGF, Ang 2, HGF, FGF, and/or VEGF). The muscle or musculofascial matrix may retain some or all of the extracellular matrix components that are found naturally in a muscle prior to decellularization, or various undesirable components may be removed by chemical, enzymatic, and/or genetic means. In general, the muscle extracellular matrix provides a structural scaffold comprising fibers, proteoglycans, polysaccharides, and growth factors into which native cells and vasculature can migrate, grow, and proliferate after implantation in a patient. The exact structural components of the extracellular matrix will depend on the type of muscle and/or fascia selected and the processes used to prepare the decellularized tissue.

In certain embodiments, the tissue sample including muscle and fascia tissue can be chemically treated to stabilize the tissue so as to avoid biochemical and/or structural degradation before, during, or after cell removal. In various embodiments, the stabilizing solution can arrest and prevent osmotic, hypoxic, autolytic, and/or proteolytic degradation;

protect against microbial contamination; and/or reduce mechanical damage that can occur during decellularization. The stabilizing solution can contain an appropriate buffer, one or more antioxidants, one or more oncotic agents, one or more antibiotics, one or more protease inhibitors, and/or one or more smooth muscle relaxants. In some embodiments, the stabilizing solution can include one or more free radical scavengers including, but not limited to, glutathione, n-acetylcysteine, superoxide dismutase, catalase, or glutathione peroxidase.

In certain embodiments, a muscle or musculofascial implant can comprise one or more additional agents. In some embodiments, the additional agent(s) can comprise an anti-inflammatory agent, an analgesic, or any other desired therapeutic or beneficial agent. In certain embodiments, the additional agent(s) can comprise at least one added growth or signaling factor (e.g., a small cell growth factor, an angiogenic factor, a differentiation factor, a cytokine, a hormone, and/or a chemokine). These additional agents can promote native muscle migration, proliferation, and/or vascularization. In some embodiments, the growth or signaling factor is encoded by a nucleic acid sequence contained within an expression vector. As used herein, the term "expression vector" refers to any nucleic acid construct that is capable of being taken up by a cell, contains a nucleic acid sequence encoding a desired protein, and contains the other necessary nucleic acid sequences (e.g., promoters, enhancers, initiation and termination codons, etc.) to ensure at least minimal expression of the desired protein by the cell.

In certain embodiments, the muscle and/or fascia tissue used to prepare a muscle or musculofascial matrix can be treated with one or more enzymes to remove undesirable antigens, e.g., an antigen not normally expressed by the recipient animal and thus likely to lead to an immune response and/or rejection. For example, in certain embodiments, muscle and/or fascia tissue can be treated with alpha-galactosidase to remove alpha-galactose (α-gal) moieties. In some embodiments, to enzymatically remove α-gal epitopes, after washing the muscle tissue thoroughly with saline, the tissue may be subjected to one or more enzymatic treatments to remove α-gal antigens, if present in the sample. In certain embodiments, the muscle and/or fascia tissue may be treated with an α-galactosidase enzyme to substantially eliminate α-gal epitopes. In addition, certain exemplary methods of processing tissues to reduce or remove alpha-1,3-galactose moieties are described in Xu et al., "A Porcine-Derived Acellular Dermal Scaffold That Supports Soft Tissue Regeneration: Removal of Terminal Galactose-α-(1,3)-Galactose and Retention of Matrix Structure" *Tissue Engineering Part A*, Vol. 15(7), 1807-1819 (2009), which is hereby incorporated by reference in its entirety.

In some embodiments, the tissue source is porcine. In alternative embodiments, the tissue source is human. In certain embodiments, the muscle tissue is harvested from skeletal muscle. A decellularized musculofascial matrix can comprise muscle tissue from one or more (e.g., 1, 2, 3, 4, 5, or more) different muscles.

While the decellularized muscle tissue in a musculofascial matrix may be derived from one or more donor animals of the same species as the intended recipient animal, this is not necessarily the case. Thus, for example, the decellularized muscle tissue may be prepared from porcine tissue and implanted in a human patient. Species that can serve as donors and/or recipients of decellularized muscle tissue include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice. In some embodiments, muscle tissue from more than one donor animal can be used.

In certain embodiments, animals that have been genetically modified to lack one or more antigenic epitopes may be selected as the tissue source for a muscle matrix. For example, animals (e.g., pigs) that have been genetically engineered to lack expression of the terminal α-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, both of which are hereby incorporated by reference in their entirety.

Muscle or musculofascial implants that include decellularized musculofascial matrices as described herein can be produced. Such implants can be used to treat various muscle defects and related disorders where repair, alteration, regeneration, and/or enhancement of muscle tissue is desired. For example, the implants can be used to treat hernias and other abdominal wall muscle injuries, where the current standard of care generally involves the use of fully decellularized dermal matrices or intact muscle transplants that are more effective in promoting fascia regeneration than regeneration of functional muscle. In another example, the implants can be used to repair a traumatic abdominal wall injury, such as from a gunshot or other blunt force injury. In yet another example, the implants can be used following the surgical removal of bulk tissue (e.g., after removal of a soft tissue sarcoma or osteosarcoma). In various embodiments, implants can be used to repair a defect in any type of skeletal muscle including, but not limited to, gluteus maximus muscle, rectus muscle, bicep femoris muscle, or gastrocnemius muscle.

In some embodiments, an implant can also be used after surgical removal of bulk muscle tissue (e.g., after surgical intervention to remove a sarcoma or osteosarcoma). For patients that do not receive an implant or that receive an implant comprising intact muscle or decellularized tissue that lacks any remaining myofibers, the rate and overall volume of muscle repair can be low. Conversely, implants according to the present disclosure can initiate and/or improve the rate and overall volume of muscle repair by inducing a sufficient (but not excessive) level of inflammation that serves to recruit the patient's muscle repair pathways (e.g., macrophage/myoblast recruitment and satellite cell activation). Similarly, in surgical procedures where muscle and/or fascia tissue is harvested from one muscle and/or fascia for transplantation into another location on the patient, implants as described herein can be placed at the harvest site to help promote the rate and overall extent of muscle and/or fascia repair at the harvest site following the transplant procedure.

In some embodiments, an implant can be used to enhance native muscle volume. For example, the implant can be used as part of a treatment for a muscle wasting disease, thereby enhancing the rate of repair and regeneration, and/or increasing the overall volume of muscle at the implant site. In another example, the implant can be used to cosmetically enhance the appearance of muscle tissue by promoting the growth of additional muscle volume at the implant site.

When an implant comprising one or more decellularized muscle matrices and/or one or more decellularized fascia matrices is used, the muscle matrix in the implant can promote muscle regeneration while the fascia matrix in the implant can promote repair or regeneration of the nearby fascia. In contrast, current surgical procedures (e.g., the use of sutures and/or implanted decellularized tissue matrices that lack myofibers) can result in repair to the fascia but minimal repair or regeneration of underlying muscle. The resulting lack of underlying muscle regeneration in current surgical procedures can lead to an increased rate of bulging, scarring, and other complications.

Several techniques in addition to or alternative to producing muscle matrix with accompanying fascia are disclosed herein to improve the strength of decellularized musculoskeletal matrices and tissue compositions. In some embodiments, the orientation of the myofibers in the tissue sample can affect the strength of the resulting tissue matrix.

In some embodiments, the tissue composition can be prepared by selecting the tissue sample such that myofibers of the decellularized musculofascial matrix are oriented in a particular direction. In some embodiments, the orientation of the cut can be the same as or different than the orientation of myofibers within the tissue.

For example, some muscles, such as the rectus muscles, tend to have myofibers oriented along the long axis or direction of force generation of the muscle; while other muscles, such as the obliques of the abdominal wall or the loin muscles can have fibers oriented obliquely or differently with respect to the long axis or direction of force generation of the muscle. In accordance with various embodiments, the orientation of the myofibers in a tissue sample can have an effect on the maximum load that a resulting tissue composition can withstand. Accordingly, in some embodiments, the present disclosure includes devices that incorporate tissue matrices formed from muscles cut into sections along selected directions. For example, the devices can include tissue matrices from muscles that are cut longitudinally or cross-sectionally, or for multi-layered devices, can include combinations of tissue matrix types.

The muscle and musculofascial implants disclosed herein can be in non-particulate form. When in non-particulate form, the implant can be in any desirable shape, e.g., a sheet, cube, sphere, or other desired shape. In some embodiments, a non-particulate muscle or musculofascial implant can have a thickness of up to about 20 mm for a single layer (e.g., about 2, 5, 10, 15, or 20 mm thick, or any thickness in between). The thickness of implants with multiple layers can depend upon the number of layers included.

Particulate implants (e.g., implants that have been cut, blended, cryofractured, or otherwise homogenized) can also be produced, and can be stored dry (e.g., lyophilized) or suspended in a gel (e.g., gelatin), hydrogel, or aqueous solution (e.g., phosphate buffered saline or any other biocompatible saline solution). Particulate implants can take the form of a powder or slurry that can be processed to have a putty-like texture that is moldable into a variety of shapes. Particulate materials can be used to produce slurry materials as discussed herein.

To improve the strength of the tissue composition, the tissue composition can comprise multiple layers of decellularized muscle. In accordance with the teachings herein, the tissue composition can contain at least some of the myofibers normally found in an unprocessed muscle sample. The tissue composition can be prepared by providing a group of muscle matrices and layering and joining the group of muscle matrices to produce a multi-layer muscle matrix.

Figure 2:
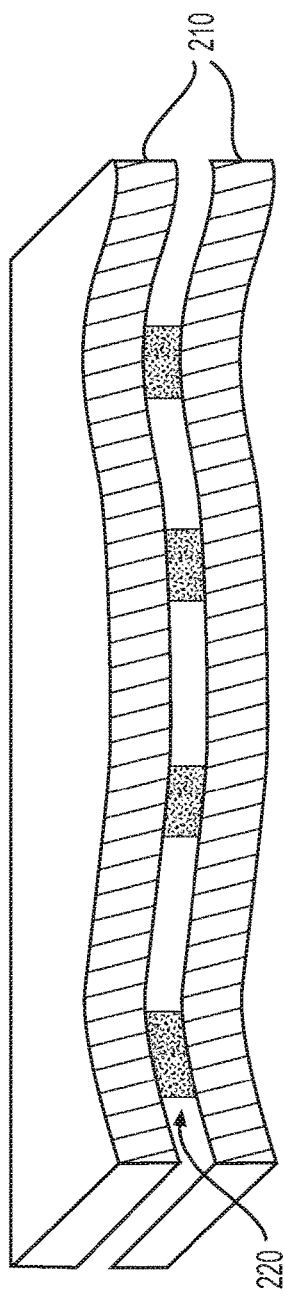
FIG. 2 illustrates a side view of a layered muscle tissue composition, according to various embodiments.

FIG. 2 is a side view of a layered muscle tissue composition 200 according to various embodiments described herein. The layered muscle tissue composition 200 can include multiple decellularized muscle matrix layers 210 that are layered and joined. In some embodiments, the layers may be joined by at least one spacer 220, but any suitable joining method can be used, including, for example, mechanical anchors, biologically compatible adhesives, or cross-linking (e.g., chemical or enzymatic joining).

The multiple decellularized muscle matrix layers 210 can be formed substantially as described above. In some embodiments, the layered muscle tissue composition 200 can include muscle matrix layers 210 that have different myofiber orientations. For example, one muscle matrix layer 210 in the layered muscle tissue composition 200 can have cross-section myofiber orientation while a different muscle matrix layer 210 can have longitudinal myofiber orientation. In some embodiments, the layered muscle tissue composition 200 can include muscle matrix layers 210 that have rotated myofiber orientations with respect to one another. For example, first and second muscle matrix layers 210 can have longitudinal myofiber orientations but with the second muscle matrix layer rotated with respect to the first muscle matrix layer such that the long axis of the myofibers in the first layer is perpendicular to the long axis of the myofibers in the second layer.

If used, the spacers 220 can be evenly spaced or irregularly spaced throughout the tissue composition. In some embodiments, the spacers 220 can be rivets, screws, staples, tacks, or any other fashioning means. In some embodiments, the spacers 220 can be biodegradable. When a layered muscle tissue composition 200 with spacers 220 such as rivets or tacks is used as part of a tissue implant during repair of abdominal wall and similar defects, the spacers 220 can provide relatively high initial load bearing capacity. Over time, the load bearing capacity can be transferred from the spacers 220 to the muscle portion of the implant (which is initially weaker) as muscle regeneration progresses and the spacer 220 degrades.

The muscle matrices can be layered and joined using a variety of techniques. In some embodiments, the group of muscle matrices 210 can be joined using dehydrothermal treatment or compression. In some embodiments, the group of muscle matrices 210 can be joined by interlocking pieces of a first muscle matrix 210 with pieces of a second muscle matrix 210. In some embodiments, the spacers 220 can comprise an adhesive, cross-linking, or denaturation agent or can comprise a tissue matrix slurry. The tissue matrix slurry can include decellularized muscle tissue, decellularized musculofascial tissue, or other decellularized tissue such as decellularized dermal tissue.

In some embodiments, the spacers 220 can comprise transglutaminase to adhere adjacent tissue matrices to one another or to other components. Transglutaminases are enzymes expressed in bacteria, plants, and animals that catalyze the binding of gamma-carboxamide groups of glutamine residues with amino groups of lysine residues or other primary amino groups. In various embodiments, transglutaminases may be used to catalyze binding of two or more muscle matrix layers to one another. In some embodiments, transglutaminases can catalyze binding of collagen in one muscle matrix layer 210 to collagen in another muscle matrix layer 210.

The layered muscle tissue composition 200 can have an increased strength compared to an individual muscle matrix layer 210. As described in greater detail below with reference to FIGS. 9 and 10, a bilayer muscle tissue composition can withstand a greater load than a single layer of muscle matrix.

Although FIG. 2 illustrates a layered muscle tissue composition 200 including two decellularized muscle matrix layers 210, one of ordinary skill in the art would appreciate that any number of muscle matrix layers could be used to form the layered composition. For example, the composition can include 2, 3, 4, 5, 6, 7, 8, 9, 10, 20, 30, 40, or 50 layers (or any number in between) depending on the desired use and needed mechanical properties.

In some embodiments, the multi-layer muscle matrix can include additional muscle matrices, supporting layers, synthetic materials, metals, other biodegradable materials, or acellular tissue matrices. In certain embodiments, the layered muscle tissue composition can include muscle matrix layers attached to supporting layers using a particulate acellular tissue matrix.

Figure 3A:
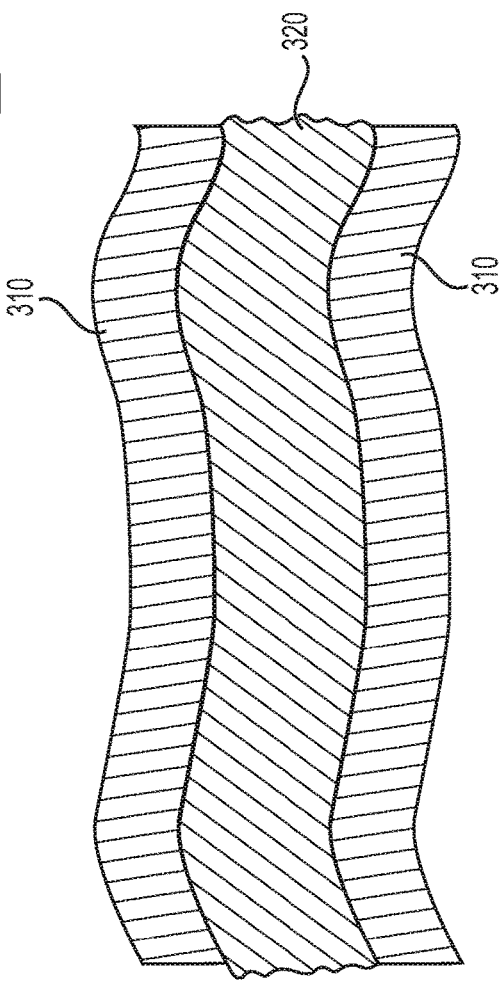
FIG. 3A illustrates a side view of a tissue composition comprising a muscle layer and a slurry according to various embodiments.

FIG. 3A is a side view of a tissue composition 300 comprising muscle matrix layers 310 and a slurry 320. The muscle matrix layer 310 may be prepared from a muscle matrix as described previously. In some embodiments, the slurry 320 can include a particulate acellular tissue matrix, including a particulate muscle matrix or other tissue matrix particulate.

Figure 3B:
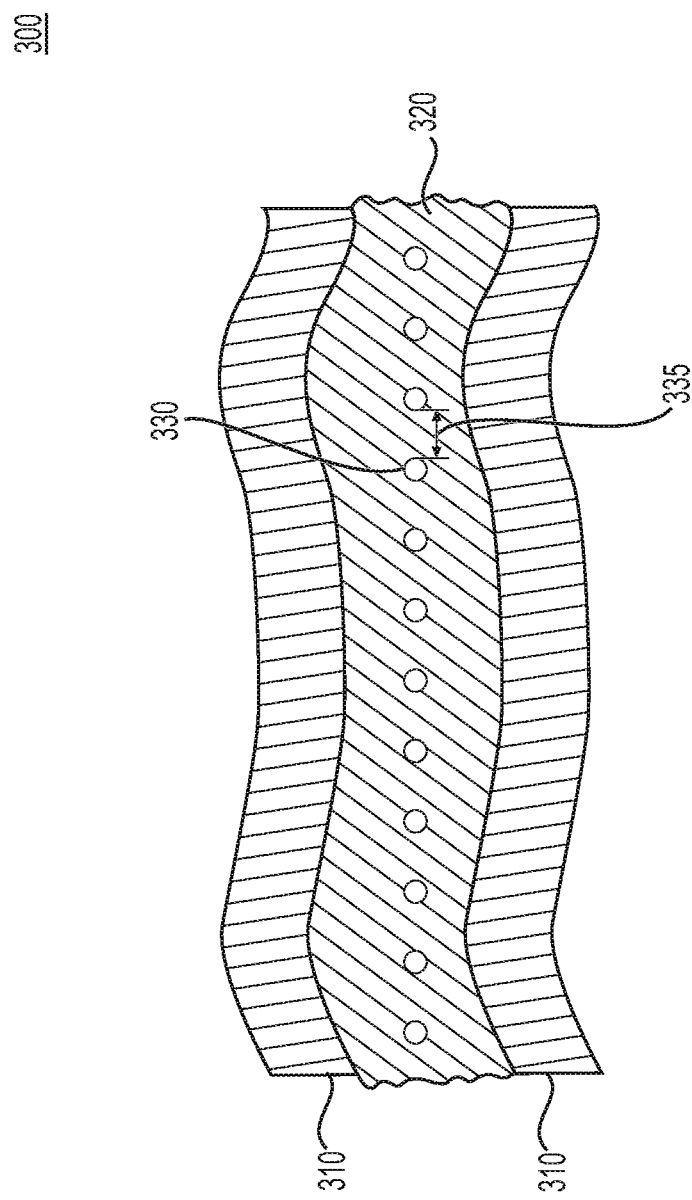
FIG. 3B illustrates a side view of a tissue composition comprising a muscle layer, a supporting layer, and a slurry according to various embodiments.

FIG. 3B is a side view of a tissue composition 300 comprising muscle matrix layers 310, supporting layer 330, and a slurry 320. The muscle matrix layer 310 may be prepared from a muscle matrix as described previously. In some embodiments, the slurry 320 can include a particulate acellular tissue matrix.

The supporting layers 330 may be any material capable of anchoring to or attached to (e.g., by being penetrated by or intermixed with pores of the layer 330) the slurry 320 including, but not limited to, metals, polypropylene, polytetrafluoroethylene, polyester, terephthalate, polyglycolide, or poly-4-hydroxybutyrate. In some embodiments, the supporting layer 330 comprises a synthetic substrate. In further embodiments, the supporting layer 330 comprises a mesh. In some embodiments, the supporting layer 330 comprises a polypropylene mesh. In certain embodiments, the supporting layer 330 can include at least one of a porous foam, a planar mesh, a multifilament woven material, a monofilament woven material, multi-leveled layers, or multi-directional layers. As shown, supporting layers is illustrated as spots, which signify cross-sectional portions of a mesh, e.g., a woven or knitted mesh, but other configurations of the supporting layer are within the scope of the supporting layer.

The supporting layer 330 can include pores or apertures 335 to improve connectivity between muscle matrix layers 310 on opposite sides of the supporting layer 330. In some embodiments, the pore size is at least 2 mm. The use of pores or apertures 335 in the supporting layer 330 can encourage tissue ingrowth into the supporting layer 330. In some embodiments, the supporting layer 330 is embedded in the tissue composition 300.

In some embodiments, the slurry 320 can be used to join the muscle matrix layers 310 to one another and/or to the supporting layer. In some embodiments, the slurry 320 can be used to join muscle matrices with supporting layers 330. In some embodiments, the particulate acellular tissue matrix (ATM) in the slurry 320 may include dermal or muscle tissue. In some embodiments, the particulate acellular tissue matrix may comprise dried particles that are rehydrated for use in the slurry 320. In further embodiments, the particulate acellular tissue matrix has a porous structure. In some embodiments, the particulate acellular tissue matrix is cross-linked or otherwise stabilized. In some embodiments, the layers 310, 320, and 330 of the tissue composition 300 are joined by compression.

The slurry 320 may be disposed on a surface of the supporting layer 330 to attach the supporting layer 330 to the muscle matrix layer 310. An additional slurry 320 may be disposed on an opposite surface of the supporting layer 330 to attach a second muscle matrix layer 310.

As described above, the tissue composition can be substantially flat or can be a flexible material that can be laid flat. Such compositions can be used in a variety of situations to allow regeneration, augmentation, support, or other treatment of tissues. However, tissue compositions as described herein may include other three-dimensional structures. In some cases, the tissue composition can include just a muscle matrix that attaches to itself.

Figure 4:
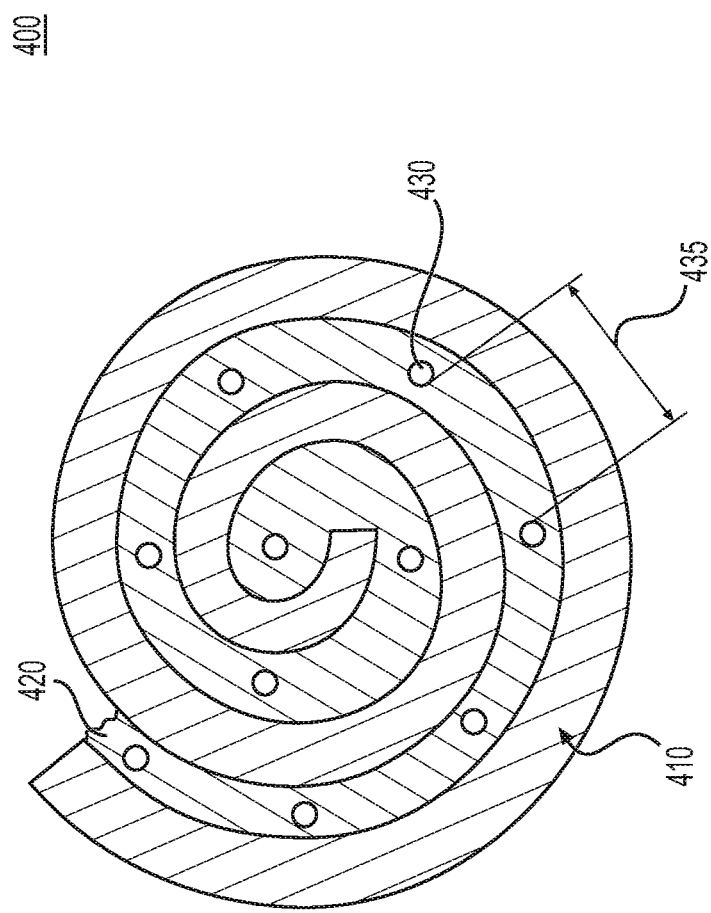
FIG. 4 illustrates a side view of a rolled tissue composition comprising a muscle layer, a supporting layer, and a slurry according to various embodiments.

As shown in FIG. 4, a tissue composition 400 can be formed from a single muscle matrix layer 410, a supporting layer 430, and a slurry 420. In accordance with various embodiments, the supporting layer 430 can include one or more pores 435. The slurry 420 and supporting layer 430 may be attached to the same side of the muscle matrix layer 410. Then, the muscle matrix layer 410 can be rolled such that the supporting layer 430 is internal to the muscle matrix layer 410. When the muscle matrix layer 410 and supporting layer 430 are rolled, a first surface of the muscle matrix layer 410 can attach to a second surface of the muscle matrix layer through the pores 435. In this way, the supporting layer 430 is not exposed to the exterior of the tissue composition 400 and the muscle matrix layer 410 can become bound to itself through the pores 435 or apertures in the supporting layer 430.

In some embodiments, the slurry 320 (or 420) can include transglutaminase (with or without particulate tissue matrix). The transglutaminases can catalyze binding of a supporting layer 330 to a muscle matrix layer 310 and/or another supporting layer 330. For example, the supporting layer 330 can be an organic or organic-derived (i.e., non-synthetic) material, and transglutaminase can cause formation of bonds between collagens of the supporting layer and muscle layer. As another example, a synthetic supporting layer 330 can be functionalized to have exposed dipeptides on the surface.

In some embodiments, the slurry 320 can include transglutaminases and particulate acellular tissue matrix. The transglutaminases can catalyze binding of individual particles of the particulate acellular tissue matrix to one another and/or with the muscle layer(s). In some embodiments, transglutaminases can catalyze binding between collagens in individual particles of the particulate acellular tissue matrix.

In accordance with the foregoing teachings, a variety of transglutaminases can be used in the slurry 320 including any that are biologically compatible, can be implanted in a patient, and having sufficient activity to provide desired catalytic results within a desired time frame. Transglutaminases can include microbial, plant, animal, or recombinantly produced enzymes. Depending on the specific enzyme used, modifications such as addition of cofactors, control of pH, or control of temperature or other environmental conditions may be needed to allow appropriate enzymatic activity. Microbial transglutaminases can be effective because they may not require the presence of metal ions, but any suitable transglutaminase may be used.

The use of transglutaminases to bind or join two or more materials can be improved by causing partial denaturation of collagen at or near the surface of the tissues, thereby making amine and acyl groups of collagen amino acids more accessible for enzymatic crosslinking. By partially denaturing collagen contained at or near the surface of a material, the denatured collagen will remain connected to the fibrillar collagen network of the tissue product, and exogenous gelatin will not be needed to assist in binding with other materials such as other tissue products or tissue at an implantation site. In accordance with various embodiments, one or more of the muscle matrix layers, supporting layers, or slurry can be subjected to a denaturation process before application of transglutaminases thereto.

The denaturation process can be performed in a number of ways. Methods for controlled denaturation of the tissue matrix collagen may include physical or mechanical processes (e.g., abrasion), thermal processes, chemical processes (e.g., acid, base or other protein denaturants), enzymatic denaturation, application of light (e.g., laser to heat or impart energy), or combinations thereof.

Although the tissue composition 300 shown in FIG. 3B includes two muscle matrix layers 310, one supporting layer 330, and two layers of particulate acellular tissue matrix slurry 320, one of ordinary skill in the art would know that any number of each of these layers could be used in combination to build up the tissue composition 300. In some embodiments, the tissue composition comprises at least one slurry 320 adjacent to the at least one supporting layer opposite the at least one muscle matrix layer. In some embodiments, the tissue composition can include at least one additional muscle matrix layer disposed adjacent to the at least one additional dry particulate acellular tissue matrix opposite the at least one supporting layer.

Muscle and/or musculofascial implants, as described above, may be packaged and/or stored as frozen, freeze-dried, hydrated, and/or dehydrated products. In certain embodiments, the packaged muscle or musculofascial implants have reduced bioburden or are sterile. In certain embodiments, a kit is provided, comprising one or more packaged muscle implant(s) and instructions for preparing and/or using the implant(s).

In some embodiments, a muscle or musculofascial implant can be treated to reduce bioburden (i.e., the implant is aseptic or sterile). Suitable bioburden reduction methods are known to one of skill in the art, and may include exposing the muscle or musculofascial implant to a compound such as acids or to radiation or the use of ethylene oxide (EO) or supercritical carbon dioxide treatments. Irradiation may reduce or substantially eliminate bioburden. In some embodiments, an absorbed dose of about 15-22 kGy of e-beam radiation is delivered in order to reduce or substantially eliminate bioburden. In various embodiments, a muscle implant is exposed to between about 5 Gy and 50 kGy of radiation (e.g., about 5, 10, 15, 20, 25, 30, 35, 40, 45, or 50 kGy, or any value in between). Suitable forms of radiation can include gamma radiation, e-beam radiation, and X-ray radiation.

The multilayer implant(s) described herein can be implanted during abdominal hernia repair. After implantation, the degree of myogenesis and fibroblast infiltration is measured and compared to myogenesis and fibroblast infiltration in the absence of an implant or in the presence of an implant comprising intact muscle or fully decellularized tissue (e.g., decellularized tissue lacking any myofibers).

Figure 5:
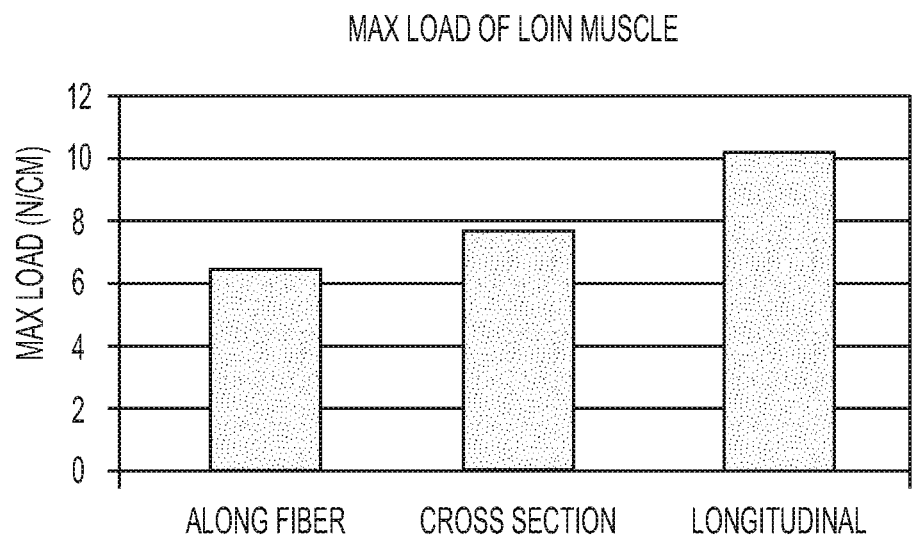
FIG. 5 is a bar graph of normalized max load values of porcine loin muscle cut in different directions and with different orientations of myofibers, according to various embodiments of the disclosed inventions.

To evaluate the effectiveness of different implants and tissue compositions, multiple types of implants were tested to measure load capacity. FIG. 5 is a bar graph illustrating the maximum load values of porcine loin muscle cut in different directions and with different orientations of myofibers. As described above, the myofibers in loin muscle are primarily oriented obliquely with respect to the long axis or direction of force generation of the muscle. Muscle cut along the myofibers demonstrated a maximum load of approximately 6 N/cm. Portions of muscle cut along the longitudinal axis of the muscle or cut cross-sectionally (i.e., perpendicular to the longitudinal axis) were also tested. It was discovered that cutting muscle along a specific orientation with respect to the myofibers increased the maximum load that could be applied to the resulting tissue. Specifically, a cross-sectional cut results in a maximum load of about 8 N/cm and a longitudinal cut results in a maximum load of about 10 N/cm. As shown by these results, implant(s) prepared using muscle with cross-sectionally oriented or longitudinally oriented myofibers may withstand a higher maximum load than muscle cut along (obliquely for loin) the myofibers.

Figure 6:
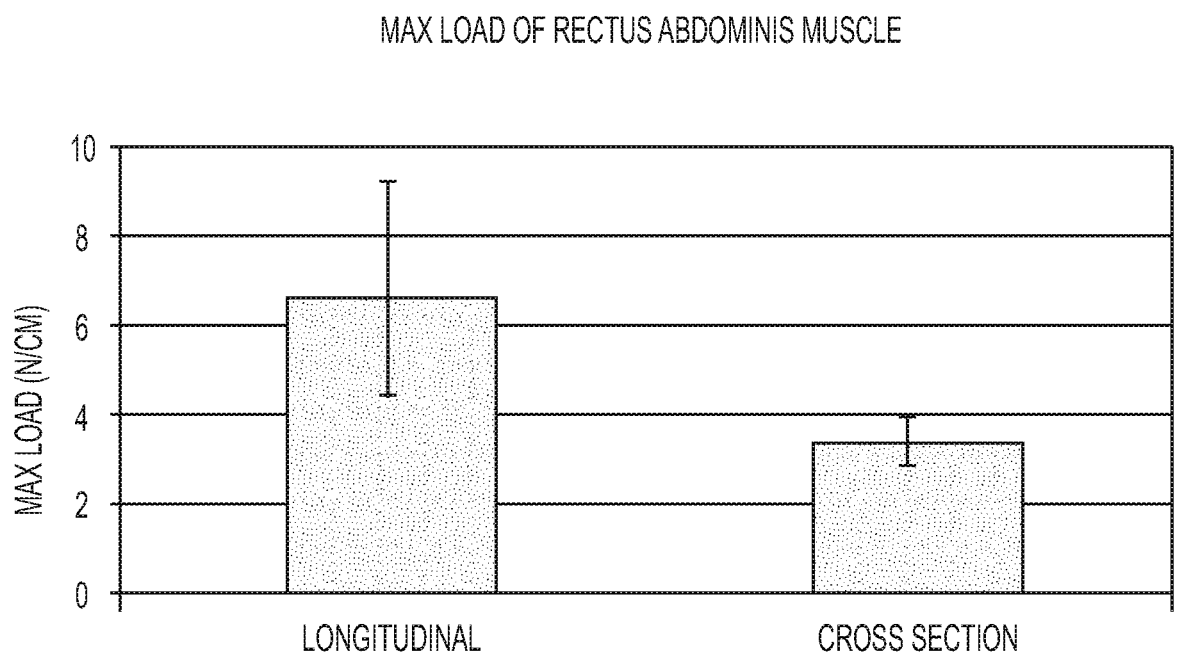
FIG. 6 is a bar graph of normalized max load values of porcine rectus abdominis muscle cut longitudinally or cross-sectionally according to various embodiments of the present disclosure.

FIG. 6 illustrates the results of testing the maximum load values of porcine rectus abdominis muscle cut along or against the myofibers. As described previously, the myofibers in rectus abdominis muscle are primarily oriented along the long axis or direction of force generation of the muscle. Muscle cut along the myofibers (i.e., along the longitudinal direction) withstood a maximum load of about 6 N/cm. Muscle cut against the myofibers (i.e., along a cross-sectional direction) withstood a maximum load of about 4 N/cm. Thus, in some embodiments, muscle cut along the myofibers may be able to withstand a higher load than muscle cut against the myofibers.

Figure 7:
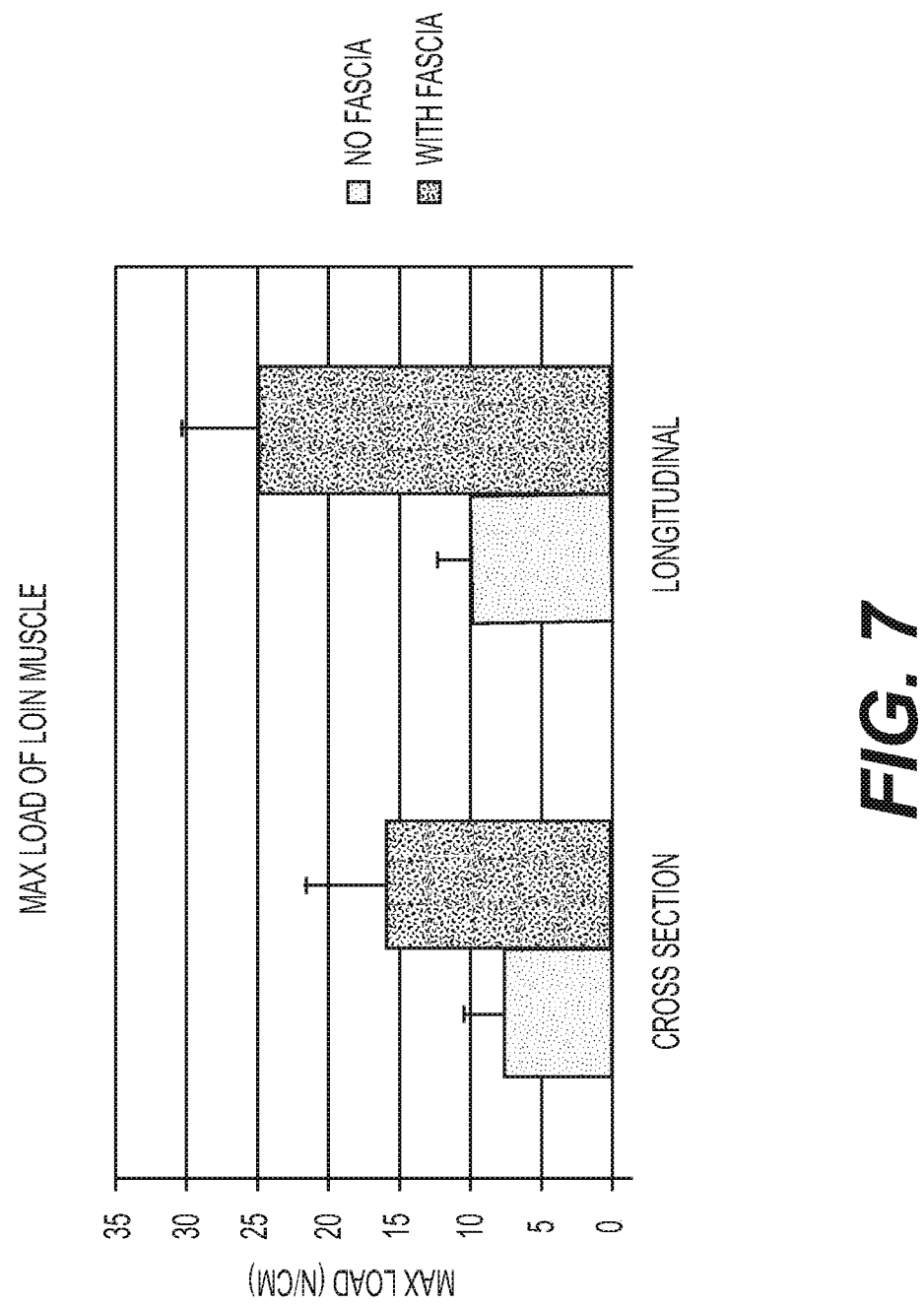
FIG. 7 is a bar graph of normalized max load values of porcine loin muscle with cross sectionally-oriented myofibers and longitudinally oriented myofibers with and without fascia according to various embodiments of the present disclosure.

FIG. 7 illustrates the results of testing the maximum load values of porcine loin muscle cut cross-sectionally and longitudinally and with and without fascia. Tissue cut along a cross-sectional direction withstood a max load of about 7.5 N/cm without fascia and about 15 N/cm with fascia. Tissue cut along a longitudinal direction withstood a max load of about 10 N/cm without fascia and 25 N/cm with fascia. In various embodiments, muscle with associated fascia attached can withstand a higher load than muscle without fascia. Additionally, muscle cut along a longitudinally oriented direction can withstand a higher maximum load than muscle cut cross-sectionally. In some embodiments, muscle with the associated fascia attached that was cut longitudinally can withstand the greatest maximum load. In some embodiments, the greater the maximum load that can be withstood by the unprocessed muscle, the greater the maximum load that can be withstood by the processed muscle matrix.

Figure 8:
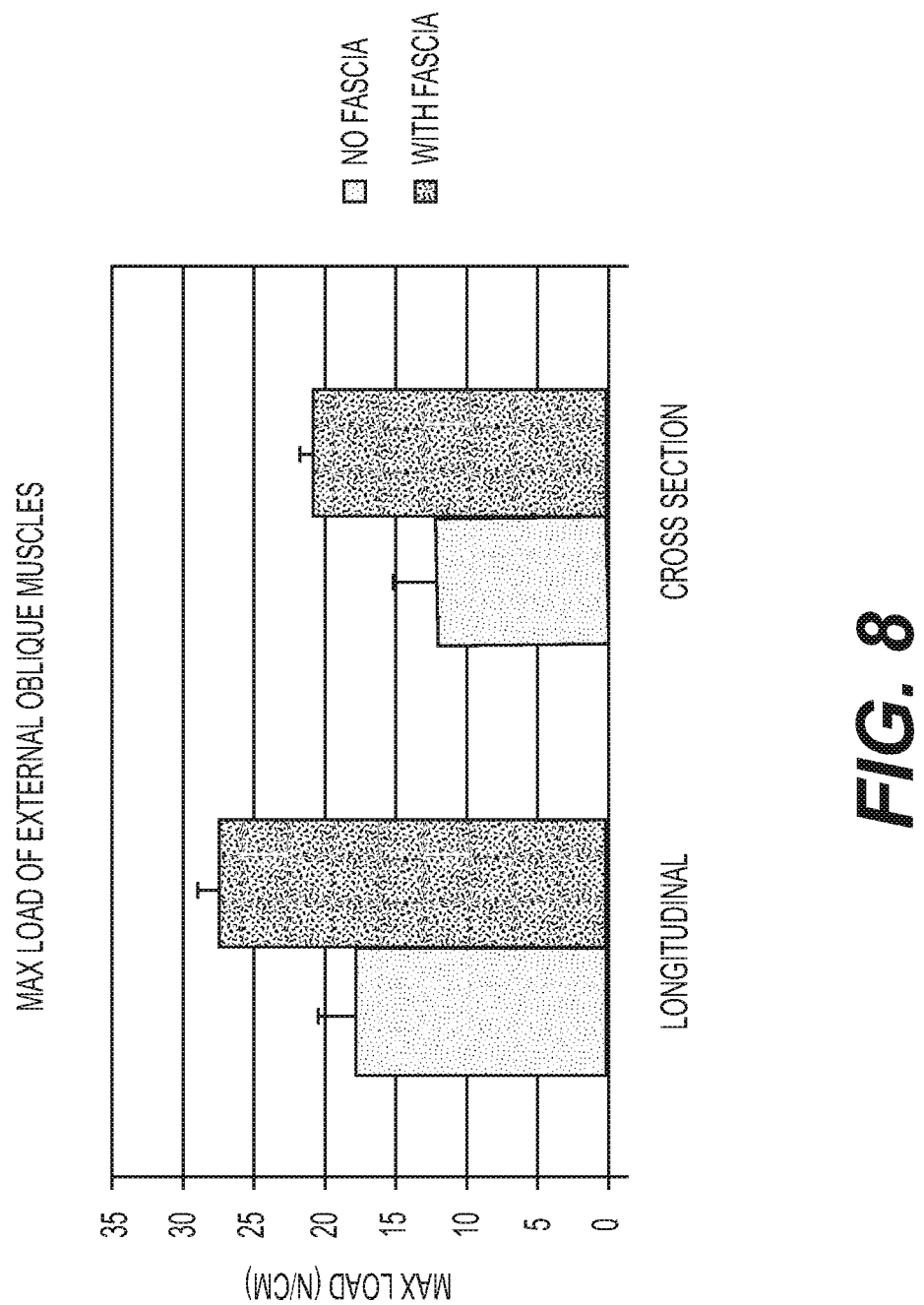
FIG. 8 is a bar graph of normalized max load values of porcine external oblique muscles cut longitudinally or cross-sectionally and with or without fascia according to various embodiments of the present disclosure.

FIG. 8 illustrates the results of testing the maximum load values of external oblique muscles cut cross-sectionally or longitudinally and with or without fascia. Tissue cut longitudinally withstood a max load of about 17.5 N/cm without fascia and about 27.5 N/cm with fascia. Tissue cut cross-sectionally withstood a max load of about 12 N/cm without fascia and 21 N/cm with fascia. In accordance with various embodiments, muscle with associated fascia attached may be able to withstand a higher load than muscle without fascia. Additionally, muscle cut longitudinally can withstand a higher maximum load than muscle cut cross-sectionally. In accordance with various embodiments, muscle with associated fascia attached that has been cut longitudinally can withstand the greatest maximum load.

Figure 9:
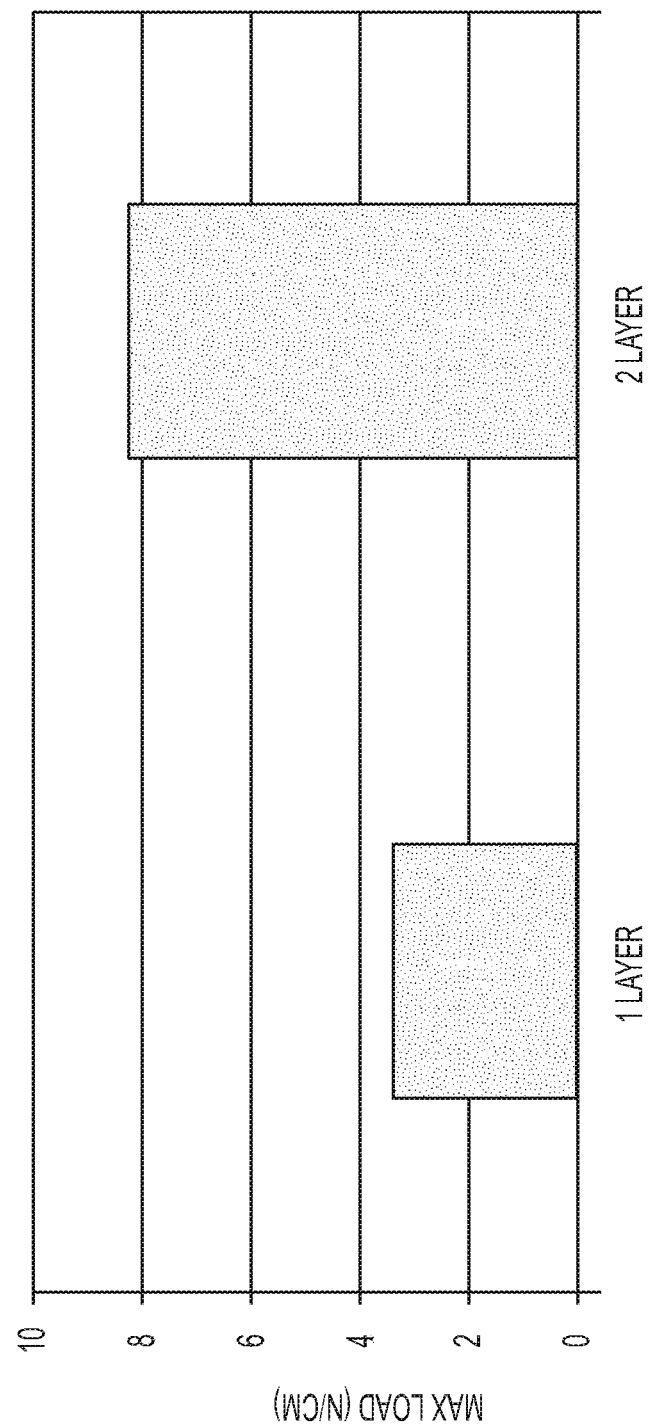
FIG. 9 is a bar graph of normalized max load values for porcine muscle matrix compositions derived from cross-sectionally cut loin muscle pieces that included a single muscle matrix layer or two muscle matrix layers according to various embodiments of the present disclosure.

FIG. 9 illustrates the results of testing the maximum load values of porcine muscle matrices comprising one layer and two layers derived from cross-sectional cut loin muscle pieces. A single layer muscle matrix withstood a maximum load of about 3.5 N/cm. Conversely, a bilayer muscle matrix withstood a max load of about 8 N/cm. In some embodiments, muscle samples comprising more than one layer of muscle matrix can withstand a greater load than samples comprising only one layer of muscle matrix.

Figure 10:
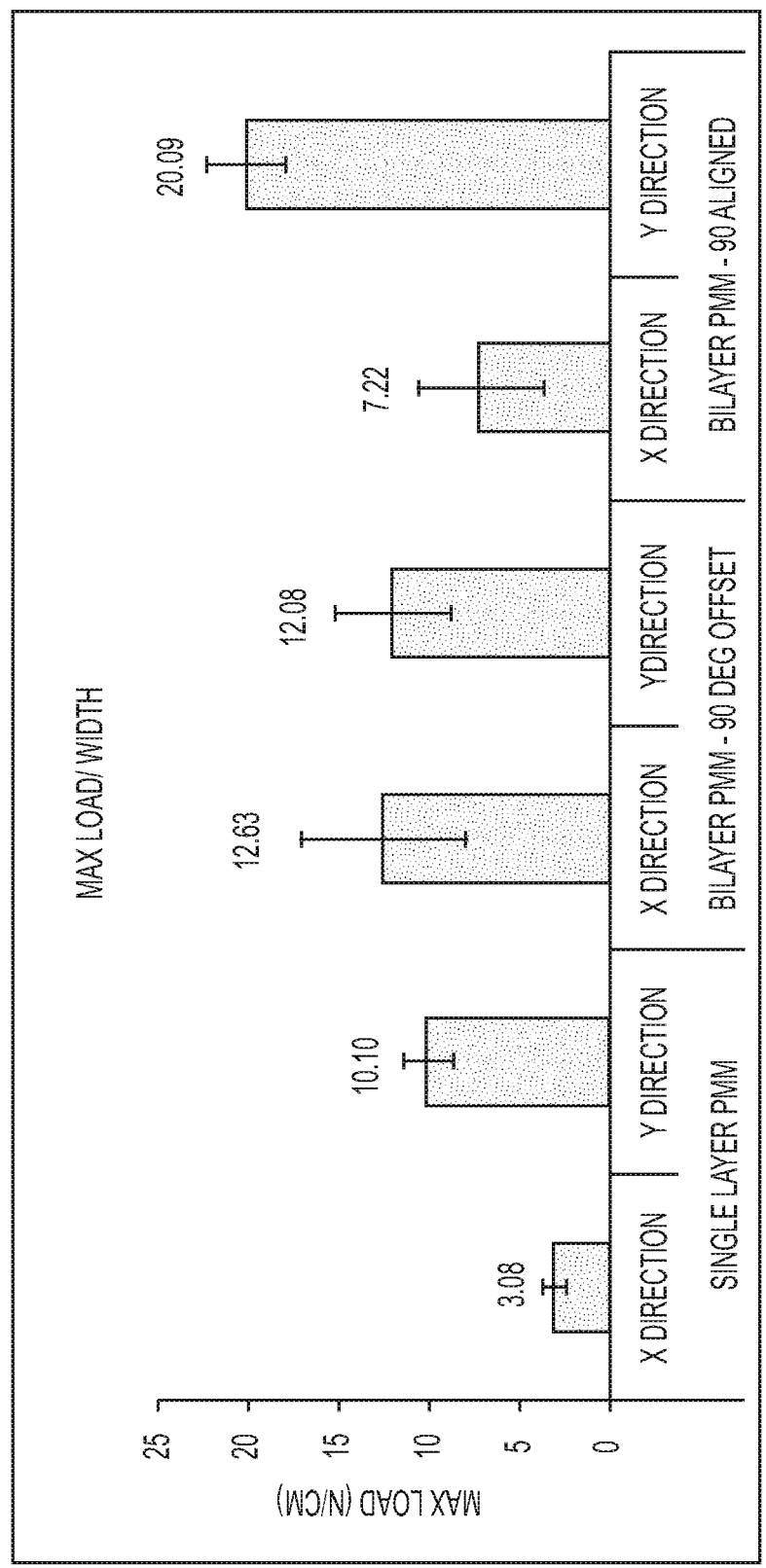
FIG. 10 is a bar graph of normalized max load values of single and bilayer porcine muscle matrix compositions derived from longitudinally cut loin muscle pieces measured in the X direction and the Y direction according to various embodiments of the present disclosure.

To determine if the strength of the muscle matrix derived from sections cut along the longitudinal orientation is equivalent in all directions, samples were tested along two perpendicular directions. FIG. 10 illustrates max load values of single and bilayer longitudinal cut porcine muscle matrix compositions measured in both X and Y directions. For single layer muscle matrices, one direction (e.g., the y-direction) yielded maximum load values that were about 3 times higher than in the other direction (e.g., the x-direction). These anisotropic results were preserved in bilayer tissue compositions produced with two muscle matrices that were aligned in the same direction. In contrast, bilayer tissue compositions produced with two muscle matrices that were rotated by 90 degrees with respect to one another showed similar maximum load values when measured in either direction. In some embodiments, anisotropy can be maintained or eliminated in multi-layer tissue compositions including muscle matrices by aligning or offsetting the cut direction in individual muscle matrices with respect to one another.

Single layer implants derived from both longitudinal and cross-sectional cut loin muscle can induce skeletal muscle repair in a gastrocnemius defect model. The data demonstrates that muscle regeneration does not depend on the myofiber orientation of the implant.

In various embodiments, an implant comprising decellularized tissue harvested from the same region of connected muscle and fascia is used. In various embodiments, the fascia portion of the decellularized tissue provides increases strength for the implant, as compared to an implant that does not comprise decellularized fascia tissue. In some embodiments, the increased strength allows the implant to better resist the tensile, torsional, and other forces the implant experiences during the regeneration process. In some embodiments, the decellularized fascia portion of the implant provides a collagen scaffold into which native cells (e.g., fibroblasts, etc.) can migrate, allowing for the remodeling of fascia along with the remodeled muscle induced by the decellularized muscle portion of the implant.

Disclosed herein are methods of making muscle and/or musculofascial implants. In various embodiments, a muscle and/or musculofascial implant comprises one or more decellularized muscle and/or fascial matrices that are prepared by selecting suitable muscle and/or musculofascial samples, washing the samples to remove red blood cells and other debris, exposing the muscle and/or musculofascial samples to trypsin, exposing the muscle and/or musculofascial samples to a decellularization solution, optionally contacting the decellularized muscle and/or musculofascial samples with DNase and/or alpha-galactosidase, washing the decellularized muscle and/or musculofascial samples, and, optionally, sterilizing the samples.

In various embodiments, the general steps involved in the production of a decellularized muscle matrix include providing a sample of muscle tissue, fascia tissue, or transition region tissue from a donor (e.g., a human cadaver or animal tissue source) and removing cellular material under conditions that preserve some or all of the biological and/or structural functions of the extracellular matrix in the sample, as well as at least some of the myofibers.

In some embodiments, a sample of muscle tissue and fascia tissue can be provided and washed to remove any residual cryoprotectants, red blood cells, and/or any other contaminants. Solutions used for washing can be any physiologically-compatible solution. Examples of suitable wash solutions include distilled water, phosphate buffered saline (PBS), or any other biocompatible saline solution.

In an embodiment, the at least one muscle sample and the least one fascia sample are contacted with a solution containing trypsin in order to break down muscle fiber bundles (e.g., by cleaving myosin molecules in the muscle fiber). In some embodiments, trypsin can facilitate the decellularization process by increasing the rate and/or extent of myofiber breakdown and myocyte removal during subsequent decellularization. In some embodiments, the muscle sample is exposed to trypsin at a concentration of about $10^{-10}$-0.5% (e.g., at about 0.02, 0.03, 0.04, 0.05, 0.06, 0.07, 0.08, 0.09, 0.1, 0.15, 0.2, 0.25, 0.3, 0.35, 0.4, 0.45, 0.5 percent, or any percentage in between). In some embodiments, the trypsin concentration can range from $10^{-8}$-$10^{-4}$%. In certain embodiments, the muscle sample is exposed to trypsin for at least about 15 minutes and/or up to a maximum of about 24 hours (e.g., about 15, 30, 45, 60, 75, 90, 105, 120 minutes, 4 hours, 8 hours, 12 hours, 24 hours or any time period in between). In certain embodiments, muscle samples including fascia can be exposed to trypsin for at least about 15 minutes and/or up to a maximum of about 48 hours (e.g., about 15 minutes, 30 minutes, 45 minutes, 60 minutes, 75 minutes, 90 minutes, 105 minutes, 120 minutes, 4 hours, 8 hours, 12 hours, 24 hours, 48 hours or any intermediate time). The length of time of trypsin exposure, and/or the concentration of trypsin, can be adjusted in order to control the extent of myofiber removal from the muscle tissue so as to retain at least some of the myofibers in the muscle sample and fascia sample after trypsinization and decellularization.

In various embodiments, the length of exposure and/or the concentration of the decellularization solution and/or trypsin solution can be adjusted in order to control the extent of myofiber removal. In some embodiments, the duration and/or concentration are selected in order to remove about 20-80% of the myofibers normally found in the muscle sample prior to trypsinization and decellularization. In certain embodiments, the duration and/or concentration are selected in order to remove about 20, 30, 40, 50, 60, 70, or 80% of the myofibers (or any percentage in between). In some embodiments, about 20-80% of the myofibers are removed by exposing the muscle tissue sample to trypsin at a concentration ranging from $10^{-10}$-0.5% for 15 minutes to 48 hours and/or by exposing the muscle tissue sample to about 0.1-2.0% of a decellularization agent (e.g., TRITON X-100™, sodium dodecyl sulfate, sodium deoxycholate, polyoxyethylene (20) sorbitan monolaurate, etc.) for 1-72 hours.

In various embodiments, about 20-80% of the myofibers normally found in a muscle sample are removed by controlling the tissue to volume ratio (e.g., the mass of tissue per volume of solution containing trypsin and/or decellularizing agents). In some embodiments, a lower tissue/volume ratio increases the efficiency of the myofiber removal process, thus resulting in a muscle matrix that retains fewer intact myofibers. In other embodiments, a higher tissue/volume ratio reduces the efficiency of the myofiber removal process, thus resulting in a muscle matrix that retains more intact myofibers.

In some embodiments, after decellularization, the muscle and/or musculofascial tissue is washed thoroughly. Any physiologically compatible solutions can be used for washing. Examples of suitable wash solutions include distilled water, phosphate buffered saline (PBS), or any other biocompatible saline solution. In some embodiments, the wash solution can contain a disinfectant. In certain, embodiments, the disinfectant is peracetic acid (PAA), for example at a concentration of 0.05, 0.1, 0.15, 0.2, 0.25, 0.3, 0.4, or 0.5% (or any percentage in between). In certain embodiments, e.g., when xenogenic or allogenic material is used, the decellularized muscle tissue is treated (e.g., overnight at room temperature) with a deoxyribonuclease (DNase) solution. In some embodiments, the tissue sample is treated with a DNase solution prepared in a DNase buffer. Optionally, an antibiotic solution (e.g., Gentamicin) may be added to the DNase solution. Any suitable DNase buffer and/or antibiotics can be used, as long as the buffer and/or antibiotic provides for suitable DNase activity.

The preceding examples are intended to illustrate and in no way limit the present disclosure. Other embodiments of the disclosed devices and methods will be apparent to those skilled in the art from consideration of the specification and practice of the devices and methods disclosed herein.

The above description and embodiments are exemplary only and should not be construed as limiting the intent and scope of the invention.

What is claimed is:

1. A tissue composition comprising:
a first muscle matrix layer and a second muscle matrix layer;
a supporting layer comprising a synthetic substrate having a first side and a second side opposite the first side; and
a first binding layer and a second binding layer, the binding layers comprising particulate acellular tissue matrix (ATM) that has been treated with a transglutaminase to attach the muscle matrix layers to the supporting layer, the first binding layer disposed adjacent to the first side of the supporting layer and adjacent to the first muscle matrix layer, the second binding layer disposed adjacent to the second side of the supporting layer and adjacent to the second muscle matrix layer.

2. The tissue composition of claim 1, wherein the synthetic substrate is a mesh.

3. The tissue composition of claim 2, wherein the synthetic substrate is a polypropylene mesh.

4. The tissue composition of claim 1, wherein the particulate ATM comprises dermal or muscle tissue matrix.

5. The tissue composition of claim 1, wherein the particulate ATM comprises rehydrated particles.

6. The tissue composition of claim 1, wherein the particulate ATM comprises a porous structure.

7. The tissue composition of claim 1, wherein the particulate ATM in the binding layer is cross-linked.

* * * * *